United States Patent [19]

Sellers, Jr.

[11] Patent Number: 5,667,790
[45] Date of Patent: Sep. 16, 1997

[54] ALUMINUM CHLORHYDRATE AS A TREATMENT FOR ACNE AND ROSACEA

[76] Inventor: Billy B. Sellers, Jr., 734 Shoreline Dr., Alexander City, Ala. 35010-9077

[21] Appl. No.: 515,061

[22] Filed: Aug. 14, 1995

[51] Int. Cl.$^6$ ............................ A61K 9/10; A61K 33/06
[52] U.S. Cl. ................... 424/401; 424/682; 424/685; 514/859
[58] Field of Search ................... 424/401, 682, 424/690, 691, 685; 514/859

[56] References Cited

U.S. PATENT DOCUMENTS

| | | | |
|---|---|---|---|
| 2,904,462 | 9/1959 | Moreland et al. | 424/690 |
| 3,842,847 | 10/1974 | Hewitt et al. | 424/70.19 |
| 3,860,705 | 1/1975 | Rubino et al. | 424/669 |
| 4,209,506 | 6/1980 | Bouillon et al. | 424/68 |
| 4,285,967 | 8/1981 | Gubernick et al. | 514/653 |
| 4,331,653 | 5/1982 | Brown et al. | 424/447 |
| 4,640,932 | 2/1987 | Fong et al. | 514/714 |
| 4,663,151 | 5/1987 | Waali | 424/685 |
| 4,734,434 | 3/1988 | Procaccini et al. | 514/535 |
| 4,762,847 | 8/1988 | Edwards et al. | 514/336 |
| 4,810,496 | 3/1989 | Jensen | 424/646 |
| 5,219,571 | 6/1993 | Wise | 424/401 |

*Primary Examiner*—Edward J. Webman
*Attorney, Agent, or Firm*—Watson Cole Stevens Davis, P.L.L.C.

[57] ABSTRACT

A method of treating skin affected by acne or rosacea includes the steps of applying to affected skin a composition containing up to 50% by weight aluminum halide salt in a liquid carrier, allowing the composition to remain on the affected skin for an extended period of time which exceeds ten minutes, and washing off the composition. The composition is preferably applied to affected skin just prior to bedtime and is allowed to remain on the skin while the patient sleeps. Alternatively, liquid make-up compositions containing up to 50% by weight aluminum halide salt are applied as a part of a daily make-up routine and allowed to remain on affected skin all day long. The methods of treatment provide an improved treatment of acne and rosacea.

19 Claims, No Drawings

ALUMINUM CHLORHYDRATE AS A TREATMENT FOR ACNE AND ROSACEA

FIELD OF THE INVENTION

The present invention relates to a treatment of skin affected by acne and rosacea.

BACKGROUND OF THE INVENTION

Acne affects a large percentage of adolescents and adults. Acne is a papillofollicular eruption of the pilosebaceous apparatus occurring primarily on facial skin of adolescent humans. Acne also commonly occurs, although to a lesser extent, on the skin of the chest and back. The onset of acne usually happens in early adolescence and may last well into adulthood. Although the exact pathogenesis of acne is unknown, its occurrence and severity may be influenced by a number of factors which include increased sebum production by sebaceous glands, the presence of bacteria, partial obstruction of the pilosebaceous canal, hormonal influences, and genetics.

Pilosebaceous follicles discharge sebum at the skin surface. During puberty, androgenic hormones influence an increase in sebum production, thus causing skin to become oily in the area of the face, chest and back. The triglycerides which comprise sebum are split into free fatty acids by lipase produced by the anaerobic bacteria *Propionibacterium acnes*. These free fatty acids, along with other bacterial products and prostaglandins, are inflammatory and chemotactic. Partial obstruction of the pilosebaceous follicle from excessive proliferation of surface epithelium allows this inflammatory mixture to remain in the canal and to leak into surrounding epidermal tissue. As a result, the acne process may cause scarring, hyperpigmentation, and cyst formation. Genetic factors may influence the time of onset, extent of severity, and pattern of this condition.

Treatments for acne have included regulating diet, application of local skin cleansers, administering local or oral antibiotics, local keratolytic agents such as benzoyl peroxide and retinoic acid, oral agents such as isotretinoin, estrogenic agents or anti-androgens which decrease sebum production or cause involution of sebaceous glands and local or intradermal anti-inflammatory agents. No single therapeutic modality has been effective in all affected individuals, and many of the presently available acne medications are expensive and may result in unacceptable lesions or sequelae. For example, keratolytic agents may cause unacceptable bleaching of the skin or may decrease skin thickness leading to an increased susceptibility to sunburn.

Local antibiotics may cause local or systemic sensitivity to the drug, thereby limiting use of that drug for more serious future infections. An increased tolerance may also develop with respect to the use of oral antibiotics. Furthermore, there is a risk of developing *pseudomembranous enterocolitis* when antibiotics are used. Isotretinoin poses well-known systemic side effects and cannot be used during pregnancy, when acne outbreaks tend to be prolific. Obvious risks also are involved with treatments based upon manipulations of hormonal balances. Many of these compositions and treatments cause skin cell bleaching which is particularly undesirable in patients having highly pigmented skin.

Although the prior art has provided means for the treatment of acne, a need remains for an inexpensive and safe treatment of acne which is effective in practically all affected individuals.

Another problematic skin condition is rosacea. Rosacea is of unknown etiology and is characterized by facial flushing, the presence of superficial red aciniform lesions, and the frequent occurrence of telangiectasia. Occasionally, and primarily in males, hyperplasia of sebaceous glands and connective tissue produces a bulbous appearance of the nose, which is known as rhinophyma. Although the exact pathogenesis of rosacea is not known, rosacea is influenced by numerous factors which include a history of seborrhea, temperature changes, dietary factors, drugs, local irritants, hormonal influences, and emotional stress.

The treatment of rosacea has parallelled the treatment of acne with often less than adequate results. Presently available therapy for rosacea involves treatment with local or systemic broad spectrum antibiotics and the avoidance of triggering factors. Avoiding triggering factors, however, is usually impractical or impossible because such factors include changes in air temperature, ingestion of particular food substances, the use of facial make-up, exposure to sun light, and numerous other common influences. Antibiotic treatment may result in the same complications as discussed above, including increased tolerance to the antibiotic, and the risk of *pseudomembranous enterocolitis*. While the prior art has provided some means for the treatment of rosacea, none of the presently available methods of treatment have proven practical and adequate.

Aluminum chlorhydrate has been used as prophylactic treatment for poison oak, poison ivy and poison sumac dermatitis, as disclosed in U.S. Pat. No. 4,663,151. However, the prophylactic composition preferably contains an alcohol/water solution carrier, and preferably is applied in anticipation of exposure. The patent makes no suggestion that the composition could treat acne or rosacea.

A need therefore exists for an inexpensive and safe treatment for rosacea which is effective for practically all affected patients.

SUMMARY OF THE INVENTION

The present invention is based upon the discovery that acne and rosacea may be effectively treated by topically applying a composition containing divided aluminum halide salt to affected areas of the skin. More particularly, the present invention is based upon the discovery of a successful treatment of acne and rosacea which includes the topical application of a composition containing up to 50% by weight aluminum halide salt, preferably aluminum chlorhydrate, in a liquid carrier agent. Compositions containing specified amounts of aluminum chlorhydrate in liquid carrier agents have proven effective according to the present invention, with no deleterious side effects.

According to an embodiment of the invention, topical compositions such as creams and gels containing a finely divided aluminum halide salt, such as aluminum chlorhydrate, are applied to affected areas of the skin each night before bedtime and washed off the next morning. Alternatively, cosmetic compositions containing an aluminum halide salt may be topically applied to affected skin and left on all day, unnoticed. The treatment is easy to perform, effective, inexpensive and safe.

DETAILED DESCRIPTION OF THE INVENTION

Aluminum chlorhydrate, $AlCl_3 \cdot 6H_2O$, is a well-known safe compound commonly used as an anti-perspirant in many commercially available preparations. Other aluminum halide salts are expected to exhibit properties similar to those of aluminum chlorhydrate and are also expected to be useful in compositions used for the treatments according to the present invention.

The methods of treatment according to the present invention are all based upon the topical application of a composition containing an aluminum halide salt, particularly aluminum chlorhydrate in a liquid carrier such as a gel, cream, lotion or liquid make-up composition. The methods include the steps of applying the topical composition to skin affected by acne or rosacea, allowing the composition to remain on the affected skin for an extended period of time which exceeds 10 minutes, and washing off the composition. In a preferred embodiment, the composition is applied and allowed to remain on the skin overnight. When formulated with a liquid make-up, the composition can be applied as part of a daily make-up routine and worn all day long.

The amount of aluminum halide salt used in the compositions is within the range of from 1 to 50 percent by weight, with a range of from one to 30 percent by weight being preferred. According to the present treatments, it has been found that aluminum halide salt concentrations of between 5 and 30 percent by weight provide compositions and treatments which are significantly effective in clinical trials. More preferably, the compositions used in the present treatment methods contain between 10 and 20 percent of weight aluminum halide salt. These ranges of concentrations are particularly suitable for compositions containing aluminum chlorhydrate.

Aluminum chlorhydrate concentrations of over 30 percent by weight result in compositions which have a gritty texture. Although compositions containing as much as 50 percent by weight can be used, the gritty consistency of such compositions make the less preferable than compositions containing 30 percent by weight aluminum chlorhydrate, or less. It has been found according to the invention that there is little advantage to increasing the concentration of aluminum chlorhydrate to greater than 20 percent by weight in the embodiments which employ aluminum chlorhydrate. At the lower end of the range, improvements in combating acne and rosacea have been found when amounts as low as 1 percent by weight are utilized.

The aluminum halide salt is preferably provided in a finely divided powdered or granular form which can be easily and homogeneously mixed with the liquid carrier agent. For example, one preferred form of an aluminum halide salt is aluminum chlorhydrate A 1087, available from Spectrum Chemical Mfg. Corp., Gardena, Calif.

The balance of the compositions used comprises a non-toxic gel, cream, lotion or liquid make-up composition and may optionally contain small effective amounts of preservative and fragrance. For example, 0.25 percent by weight phenol may be used as a preservative and 0.25 percent by weight peppermint oil may be used as a fragrance additive. In a preferred embodiment, the invention consists essentially of these components.

The carrier agent is herein referred to as a liquid carrier agent and includes creams, gels, lotions and liquid make-up compositions. Liquid carrier agents are used for a number of reasons, which include providing an easy application, good flowability, homogeneous mixing of the aluminum halide salt in the agent, and good penetration into the skin and pores. At least 50% by weight of the compositions used in accordance with the present methods comprise a liquid carrier agent. More preferably, between about 70 and 95% by weight liquid carrier agent is used, with the range of between 80 and 90% by weight being even more preferred.

Particularly useful liquid carrier agents include aqueous gels, oil-based creams, and various brands of commercially available facial make-up. Specific examples of useful liquid carrier agents include: moisturizing lotions; facial skin oils; aqueous-based skin conditioners; gels containing purified water, hydroxypropyl methylcellulose, glycerin, propylene glycol, sodium phosphate, boric acid, diaolidinyl urea, methyl paraben, propylparaben, and potassium sorbate (such as Liqua-Gel™ available from Paddock Laboratories, Minneapolis, Minn.); creams containing partially hydrogenated soybean and cottonseed oils, mono- and di-glycerides (such as Crisco™ available from Proctor and Gamble, Cincinnati, Ohio); and liquid make-up (such as Moisture-Silk Liquid Makeup™ available from Frances Denny Corp. Dist., New York, N.Y.).

When a gel is used, it is believed that some of the aluminum halide salt is dissolved in the gel. This is particularly suspected with the use of aluminum chlorhydrate. When oil-based creams are used, it is believed that the aluminum halide salt is homogeneously dispersed throughout the cream with little or no dissolution. With either gel or cream carriers, the finely divided aluminum halide salt readily penetrates and is absorbed into the pores and through the cornified layer of the skin. The use of at least 50 percent by weight gel or cream, more preferably at least 70 percent by weight gel or cream, enables a topically applicable composition which can be applied uniformly to the skin and which provides a ready adsorption and penetration of aluminum halide salt.

Although it is expected that aluminum halide salts in general will provide beneficial effects according to the treatments of the present invention, the use of aluminum chlorhydrate has proven particularly useful. Other particularly useful aluminum halide salts include aluminum chloride and aluminum bromide. It is expected that the same concentrations of aluminum chloride or aluminum bromide, as those of aluminum chlorhydrate, would be effective against acne and rosacea.

The treatment methods of the present invention employ a composition which can reach the sebaceous glands to decrease the activity of oil production therefrom and decrease the superficial blood flow through the various layers of skin. The compositions used according to the present methods further provide antibacterial effectiveness, drying action, and a decrease in facial lines and skin wrinkling especially in older individuals. These present advantages are achieved without thinning the skin, without increasing the likelihood of sunburn, and without bleaching melanin or skin cells in general.

The treatments according to the present invention are also extremely helpful to patients affected by rosacea, which is more common in middle aged and older women. To disguise the condition, many patients apply make-up, which further complicates their condition as make-up is a triggering factor for outbreaks of rosacea. According to the present invention, treatments are provided wherein aluminum halide salt is added to liquid make-up compositions such that the beneficial effects are two-fold: make-up can be worn without fear of a rosacea outbreak; and the make-up itself can be used to treat the condition all day long.

The present invention may be more fully understood with reference to the examples set forth below.

EXAMPLES

Three liquid carrier agents were used to formulate compositions for the treatment of acne and rosacea according to the present invention. The agents were (1) Liqua-Gel™ an aqueous gel, (2) Crisco™ an oil-based cream, and (3) various brands of commercially available facial liquid makeup. Different concentrations of aluminum chlorhydrate were used on a variety of subjects as shown in Table I below. In addition, 0.25 percent by weight phenol and 0.25 percent by weight oil of peppermint were added to both the gel and cream preparations.

Treatment subjects were instructed to wash their face with soap and water and dry the facial skin. The compositions used according to the present invention were then applied, either at bedtime as in the case of the gels and creams, or as a facial make-up in the morning. The night-time gel and cream medications were left on over-night and then washed off the next morning. The day-time make-up medication was left on during the day and washed off in the evening. In both studies, treatment was carried out on a daily basis for a minimum treatment period of one month. Evaluation of efficacy was performed by both the subject and a neutral investigator. As can be seen from Tables I and II below, all patients showed improvement in conditions of acne and rosacea, respectively.

TABLE I

ACNE TREATMENT

| Carrier | Concentration | No. Subjects | Results |
|---|---|---|---|
| Gel | 1% | 2 | 100% w/moderate improvement |
|  | 5% | 4 | 100% w/moderate improvement |
|  | 10% | 14 | 100% with major improvement |
|  | 20% | 44 | 100% with major improvement |
|  | 30% | 4 | 100% with major improvement |
| Cream | 5% | 4 | 100% w/moderate improvement |
|  | 10% | 4 | 100% with major improvement |
|  | 20% | 4 | 100% with major improvement |
| Make-up | 10% | 6 | 100% w/moderate improvement |

TABLE II

ROSACEA TREATMENT

| Carrier | Concentration | No. Subjects | Results |
|---|---|---|---|
| Gel | 1% | 2 | 100% w/moderate improvement |
|  | 5% | 2 | 100% w/moderate improvement |
|  | 10% | 2 | 100% with major improvement |
|  | 20% | 5 | 100% with major improvement |
|  | 30% | 1 | Major improvement |
| Cream | 10% | 2 | 100% w/moderate improvement |
|  | 20% | 4 | 100% w/moderate improvement |
| Make-up | 10% | 6 | 100% with major improvement |

To grade the improvement of acne and rosacea conditions of the various patients after treatment, a scale was used which rated improvement progressively from no improvement to major improvement, with mild improvement and moderate improvement falling respectively in between. As can be seen from the results in the tables above, all patients showed better than mild and at least moderate improvement in their respective conditions. Compliance with the treatment instructions was variable but generally good. Some variability in the protocol occurred when subjects used the test substance in a manner different from that recommended. The most common variability occurred when subjects failed to apply the test substance at night, and instead applied the test substance for only approximately 15 to 30 minutes in the morning. Significant improvement was reported even after the short interval. No adverse reactions were noted by subjects during the time of use. All subjects elected to continue the treatment at the end of one month.

One adult male subject who was not a part of the studies above found an improvement in his acne condition by using a 20% concentration of aluminum chlorhydrate in the Liqua-Gel™, and treating only once every third day.

Although the present invention has been described in connection with preferred embodiments, it will be appreciated by those skilled in the art that additions, modifications, substitutions and deletions not specifically described may be made without departing from the spirit and scope of the invention defined in the appended claims.

What is claimed is:

1. A method of treating skin affected by acne or rosacea, said method comprising the steps of:

providing a composition for the treatment of acne and rosacea which includes an active ingredient dispersed in at least 50% by weight non-toxic liquid carrier agent, said active agent consisting essentially of 0.1 to 50% by weight finely divided aluminum halide salt, topically applying said composition to an area of skin affected by acne or rosacea allowing said composition to remain on the affected area for a period of time exceeding ten minutes; and washing off said composition from the affected area.

2. A method as defined in claim 1, wherein said affected skin is facial skin.

3. A method as defined in claim 1, wherein said composition comprises between 5% and 30% by weight said aluminum halide salt.

4. A method as defined in claim 1, wherein said composition comprises between 10 and 20% by weight said aluminum halide salt.

5. A method as defined in claim 4, wherein said composition comprises between 80 and 90% by weight said liquid carrier agent.

6. A method as defined in claim 1, wherein said composition consist essentially of between 10 and 20% by weight said aluminum halide salt and between 80 and 90% by weight said liquid carrier agent.

7. A method as defined in claim 1, wherein said composition is applied prior to bedtime and is washed off after a period of sleep.

8. A method as defined in claim 1, wherein said liquid carrier agent comprises a liquid facial make-up, and said composition is applied as part of a daily make-up routine and remains on the affected skin during the day.

9. A method as defined in claim 1, wherein said steps of applying and washing off are repeated every day for at least one month.

10. A method as defined in claim 1, wherein said steps of applying and washing off are repeated every day.

11. A method as defined in claim 1, wherein said liquid carrier agent is at least one member selected from the group consisting of aqueous gels, oil-based creams, liquid make-up compositions, and skin lotions.

12. A method as defined in claim 1, wherein said liquid carrier agent is selected from the group consisting of partially hydrogenated soybean oils, cottonseed oils, monoglycerides and diglycerides.

13. A method as defined in claim 1, wherein said liquid carrier agent is selected from the group consisting of purified water, an aqueous gel containing hydroxypropyl methylcellulose, glycerin, and propylene glycol.

14. A method as defined in claim 1, wherein said composition further comprises an effective amount of phenol as a preservative.

15. A method as defined in claim 1, wherein said composition comprises about 0.25% by weight phenol.

16. A method as defined in claim 1, wherein said composition further comprises an effective amount of fragrance.

17. A method as defined in claim 1, wherein said composition comprises about 0.25% by weight fragrance.

18. A method as defined in claim 1, wherein said aluminum halide salt is aluminum chlorhydrate.

19. A method as defined in claim 18, wherein said composition comprises between 10 and 20% by weight said aluminum chlorhydrate.

* * * * *